United States Patent [19]

Sircar et al.

[11] 4,261,997

[45] Apr. 14, 1981

[54] 4-ALKYL-PYRAZOLO[5,1-B]-QUINAZOLIN-9(4H)-ONES AND ANTI-ALLERGIC COMPOSITIONS CONTAINING THEM

[75] Inventors: Jagadish C. Sircar, Ann Arbor; Stephen J. Kesten, Ypsilanti, both of Mich.

[73] Assignee: Warner-Lambert Company, Morris Plains, N.J.

[21] Appl. No.: 111,160

[22] Filed: Jan. 11, 1980

Related U.S. Application Data

[63] Continuation-in-part of Ser. No. 6,045, Jan. 24, 1979, abandoned.

[51] Int. Cl.³ .................. A61K 31/505; C07D 487/04
[52] U.S. Cl. ...................................... 424/251; 544/250
[58] Field of Search ........................ 544/250; 424/251

[56] References Cited

U.S. PATENT DOCUMENTS

| | | | |
|---|---|---|---|
| 3,150,136 | 9/1964 | Wolfram et al. | 544/250 |
| 3,157,655 | 11/1964 | Takamizawa et al. | 544/281 |
| 3,167,537 | 1/1965 | Menzel et al. | 544/250 X |
| 3,887,559 | 6/1975 | Hardtmann | 544/250 |
| 4,017,625 | 4/1977 | Kadin | 424/251 |
| 4,033,961 | 7/1977 | Schwender et al. | 544/252 |
| 4,112,098 | 9/1978 | Vogt | 424/251 |

OTHER PUBLICATIONS

Menzel et al., Chemical Abstracts, vol. 56, 4904g (1962).

*Primary Examiner*—Donald G. Daus
*Assistant Examiner*—Diana G. Rivers
*Attorney, Agent, or Firm*—Stephen I. Miller

[57] ABSTRACT

Certain pyrazolo[5,1-b]quinazolin-9(4H)-ones are disclosed. These compounds prevent the allergic response in mammals.

13 Claims, No Drawings

4-ALKYL-PYRAZOLO[5,1-b]-QUINAZOLIN-9(4H)-ONES AND ANTI-ALLERGIC COMPOSITIONS CONTAINING THEM

CROSS REFERENCE TO RELATED APPLICATION

This application is a continuation-in-part of our application serial number 006,045, filed Jan. 24, 1979 now abandoned.

BACKGROUND OF THE INVENTION

U.S. Pat. Nos. 3,150,136 and 3,167,537 discloses, inter alia certain pyrazoloquinazolone carboxylic acids which are useful as intermediates for the preparation of dyestuffs. German Pat. No. 1,111,505 discloses substituted 2-carboxy-pyrazolo-[5,1-b]quinazolin-9(4H)-ones which are useful as photographic color developers. The references do not disclose any pharmaceutical utility for these acids, nor do they disclose the tetrazoles of the present invention.

SUMMARY OF THE INVENTION

The present invention relates to a compound of the formula I:

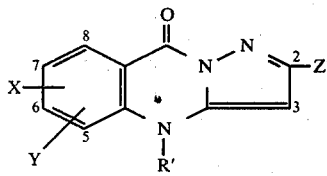

wherein X is hydrogen, hydroxy, alkyl of from 1 to 6 carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is alkyl of from 1 to 6 carbon atoms; Z is COOH or

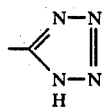

and the pharmaceutically acceptable salts thereof.

The invention also relates to a pharmaceutical composition comprising an anti-allergic effective amount of a compound of the formula I:

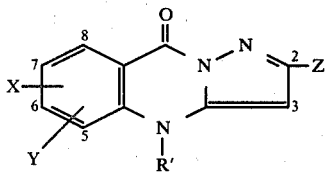

wherein X is hydrogen, hydroxy, alkyl of from 1 to 6 carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is alkyl of from 1 to 6 carbon atoms; Z is COOH or

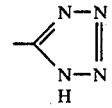

and the pharmaceutically acceptable salts thereof.

The invention also relates to a method of preventing the allergic response in a mammal which comprises administering to said mammal an anti-allergic effective amount of a compound of formula I and the pharmaceutically acceptable salts thereof.

DESCRIPTION OF THE INVENTION

The tetrazoles of the invention, i.e., compounds of the formula I wherein Z is

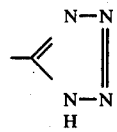

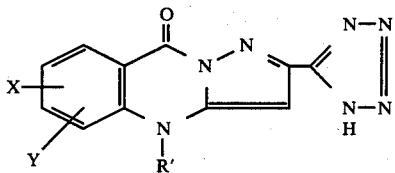

and X, Y and R' are as defined above may be prepared from the corresponding acids or esters by methods familiar to those skilled in the art. For example, the properly substituted carboxylic acid may be converted to the corresponding acid halide such as the chloride by treatment with thionyl chloride or oxalyl chloride and converted to the acid amide by treatment with ammonia. The amide is dehydrated by treatment with, for example, phosphorous oxychloride or thionyl chloride in dimethylformamide thereby producing the corresponding nitrile which when treated with sodium azide and ammonium chloride, for example, will yield the corresponding tetrazole. The above-described amides may also be prepared directly from the corresponding esters by treatment with, for example, gaseous ammonia by methods familiar to those skilled in the art.

Other methods and reagents for converting carboxylic acids or esters into the corresponding tetrazoles will be familiar to those skilled in the art.

The above-described 2-carboxy-4-alkyl-pyrazolo-[5,1-b]quinazolin-9(4H)-ones may be prepared by alternate procedures, which are considered equivalent for purposes of the invention. In one such procedure a 3-alkoxycarbonyl-2-pyrazolin-5-one having formula II

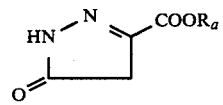

wherein $R_a$ is any convenient alkyl group, preferably of from 1 to 6 carbon atoms, most preferably ethyl is reacted in the presence of a strong base such as sodium hydride with a substituted N-alkyl isatoic anhydride of formula III

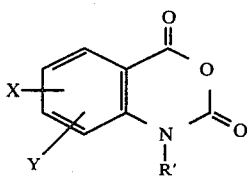

III producing a 4-alkyl-4,9-dihydro-9-oxo-pyrazolo[5,1-b]-quinazoline-2-carboxylic acid ester having formula IV

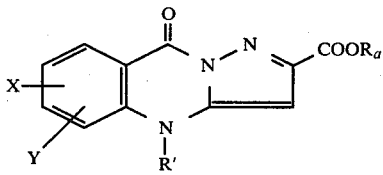

IV wherein X, Y, R' and $R_a$ are as defined above. The ester function of the compound of formula IV may be hydrolyzed by any convenient procedure to produce the corresponding acid, i.e., the compound of formula I wherein Z is COOH.

The 3-alkoxycarbonyl-2-pyrazolin-5-ones of formula II may be prepared by the procedure of R. V. Rothenberg, J. Prakt. Chem., 2, 53 (1895).

The substituted N-alkyl isatoic anhydrides of formula III may be prepared by the procedure of G. E. Hardtmann, et al., J. Hetero. Chem., 12, 565 (1975); these compounds may also be prepared by alkylating the corresponding N-unsubstituted isatoic anhydride which themselves may be prepared for example, by reacting a properly substituted anthranilic acid with phosgene. Several of these compounds are also commercially available from the Aldrich Chemical Company, Milwaukee, Wisconsin and the Sherwin Williams Company, Cleveland, Ohio.

The alkylthio anthranilic acids which are utilized to prepare the corresponding alkylthio substituted isatoic anhydrides are novel, and may themselves be prepared by alternate procedures which are considered equivalent for purposes of the invention. One such procedure involves the steps of treating a halo-substituted 2-nitrobenzoic acid with sodium sulfide; alkylating the so produced mercaptan; followed by reduction of the nitro group thereby producing the desired alkylthio substituted anthranilic acid. The above-described alkylated mercaptan may also be produced by treating the halo-substituted 2-nitrobenzoic acid with a mercaptide such as a sodium mercaptide. The starting halo-substituted 2-nitrobenzoic acids are either commercially available or may be prepared by methods known to those skilled in the art. For example, 5-chloro-2-nitrobenzoic acid is available from Aldrich Chemical Company, Milwaukee, Wisconsin 53233. J. Pharm. Soc. Japan, 72, 76 (1952), [C.A.: 46, 11150h (1952)] discloses ethyl 5-ethylthio anthranilate.

In an alternate procedure, a 2-carboxy(or 2-carboalkoxy)pyrazolo[5,1-b]quinazoline-9(4H)-one of the formula V

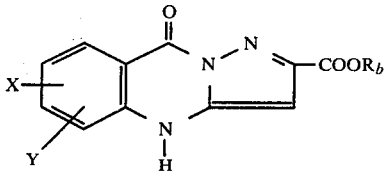

V

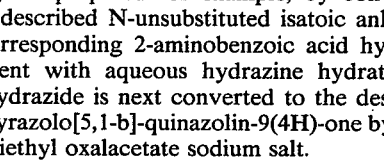

wherein X and Y are as defined above and $R_b$ is hydrogen or alkyl of from 1 to 6 carbon atoms may be alkylated by standard procedures to produce the corresponding 4-alkyl derivative. The compounds of formula V may be prepared for example, by converting the above-described N-unsubstituted isatoic anhydrides to the corresponding 2-aminobenzoic acid hydrazide by treatment with aqueous hydrazine hydrate solution. The hydrazide is next converted to the desired 2-carboxypyrazolo[5,1-b]-quinazolin-9(4H)-one by treatment with diethyl oxalacetate sodium salt.

The compounds of the invention of formula I are acids or are acidic in nature and form pharmaceutically acceptable salts with both organic and inorganic bases such as dimethylaminoethanol, the alkali metal and alkaline earth hydroxides and the alkali metal carbonates and bicarbonates such as lithium, sodium, potassium and calcium hydroxide, and the carbonates and bicarbonates of lithium, sodium and potassium. The salts are prepared by reacting an acid or the tetrazole with the desired base in the conventional manner. The tetrazoles and acids differ from their respective salts somewhat in certain physical properties such as solubility in polar solvents, but the salts are otherwise equivalent to their respective tetrazoles or acids for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The alkylthio groups, alkoxy groups and alkyl groups contemplated by the invention comprise both straight and branched carbon chains of from 1 to 6 carbon atoms. Representative of such groups are methyl, ethyl, isopropyl, pentyl, 3-methylpentyl, methoxy, ethoxy, propoxy, 1-ethylbutoxy, pentoxy, methylthio, isopropylthio, n-butylthio and the like. The term halo is intended to include fluorine, chlorine, bromine and iodine.

The compounds of the invention of formula I are new chemical substances of value as pharmacological agents which prevent the allergic response in mammals by inhibition of the release of such allergic mediators, as histamine. The assay by which this utillity was established is carried out as follows.

Rat Reaginic Passive Cutaneous Anaphylaxis (PCA).

The PCA test (D. J. Herzig, P. R. Schumann, E. J. Kusner, L. Robichaud, R. E. Giles, G. Dubnick, M. von Strandtmann, S. Klutchko, M. Cohen, and J. Shavel, Jr., "Immunopharmacology", M. E. Rosenthale and H. C. Mansmann, Eds., Spectrum Publications, Inc., New York, N.Y., 1975, pp. 103–124) involved immunization of rats with 1 mg of ovalbumin intramuscularly and approximately $10^{10}$ B. pertussis organisms as pertussis vaccine, intra-peritoneally. Fourteen days later, the rats were bled and the serum was prepared. Suitable dilutions of antiserum were injected intradermally at various sites on the back of rats 48 hrs before an intravenous injection of 1 mg of ovalbumin in 1 ml of physiological saline and 0.25% Evans Blue. Thirty minutes later the animals were killed in ether, the dorsal skin was reflected, and the mean orthogonal diameter of the wheal was measured. For oral or intraperitoneal dosing, the drugs were suspended in 1% gum tragacanth in physiological saline and given 10–15 min before intra-venous antigen challenge. For intravenous dosing, the compounds were dissolved in the saline/ovalbumin/ Evans Blue solution and given with the antigen. If necessary, the compounds were first dissolved in a slight molar excess of sodium bicarbonate and then diluted into the antigen solution. Groups of five animals were used for all dose levels and control groups.

To quantitate the PCA test, the mean diameter of each wheal spot was graphed as a function of the relative anti-serum concentration. The line, fitted by the least-squares equation, was extrapolated to the value at "zero" antiserum concentration (base value). The following equation was then used to calculate the percent inhibition:

$$\left[1 - \left(\frac{\text{diameter of drug} - \text{base value}}{\text{diameter of control} - \text{base value}}\right)\right] \times 100$$

The statistical significance of the results was determined by Student's t test (p ≦0.05). An inhibition of 15% was significant.

Test results obtained for several preferred compounds of the invention are as follows: 4-methyl-7-methoxy-2-(1H-tetrazol-5-yl)-pyrazolo-[5,1-b]quinazo-lin-9(4H)one shows a 100% inhibition of allergic response when administered intravenously to the rat at a dose of 0.1 mg/kg; 4,9-dihydro-7-methoxy-4-methyl-9-oxopyrazolo[5,1-b]quinazoline-2-carboxylic acid shows a 57% inhibition of the allergic response when administered intravenously to the rat at a dose of 0.1 mg/kg; 4,9-dihydro-4-methyl-9-oxopyrazolo[5,1-b]-quinazoline-2-carboxylic acid shows a 100% inhibition of the allergic response when administered intra-venously to the rat at a dose of 0.5 mg/kg; 4,9-dihydro-6,7-dimethoxy-4-methyl-9-oxopyrazolo[5,1-b]quinazoline-2-carboxylic acid shows a 100% inhibition of the allergic response when administered intraperitoneally to the rat at a dose of 5 mg/kg; 4,9-dihydro-5-methoxy-4-methyl-9-oxo-pyrazolo[5,1-b]quinazoline-2-carboxylic acid shows a 60% inhibition of the allergic response when administered intraperitoneally to the rat at a dose of 5 mg/kg; 4,9-dihydro-9-oxo-5-propoxy-4-propyl-pyrazolo[5,1-b]-quinazoline-2-carboxylic acid shows a 72% inhibition of the allergic response when administered intra-peritoneally to the rat at a dose of 5 mg/kg.

The compositions of the invention can be administered in a variety of dosage forms such as tablets or capsules and liquids for oral or parenteral use. The dosage forms may contain, in addition to the active component, any of the usual compounding excipients such as flavors, colors, stabilizers and tableting materials such as binders, fillers, lubricants and the like. The dosage requirements may vary with the particular composition being employed and may depend on the severity of the symptoms being presented and the size of the mammal being treated. In general, an amount of from about 0.1 to about 10 mg/kg of the active component in single or divided doses will be sufficient to accomplish the method of the invention. The invention is illustrated by the following examples.

EXAMPLE 1

4-Methyl-2-(1H-tetrazol-5-yl)pyrazolo[5,1-b]-quinazo-lin-9(4H)-one

A mixture of 2.25 g of 4,9-dihydro-4-methyl-9-oxo-pyrazolo[5,1-b]quinazoline-2-carbonitrile, 1.9 g of sodium azide, 1.5 g of ammonium chloride and 350 ml of dimethylformamide is stirred and heated at 100° C. for 20 hours, then evaporated at reduced pressure. The residue is stirred with 1 liter of diluted hydrochloric acid and the resulting solid is collected by filtration. The solid is stirred with excess saturated aqueous sodium carbonate and the solution is clarified by filtration. The filtrate is acidified with dilute hydrochloric acid and the resulting precipitate of 4-methyl-2-(1H-tetrazol-5-yl)pyrazol[5,1-b]quinazolin-9(4H)-one is collected by filtration, washed with water and dried; mp 323° C. (dec), after crystallization from dimethylformamide/ethanol.

A sample of the above tetrazole is dissolved in an aqueous solution of one equivalent of sodium hydroxide. The solution is clarified by filtration and freeze-dried to give a residue of the sodium salt. By substituting potassium hydroxide, calcium hydroxide or magnesium hydroxide for sodium hydroxide, one can obtain the potassium, calcium or magnesium salt, respectively.

EXAMPLE 2

7-Chloro-4-methyl-2-(1H-tetrazol-5-yl)pyrazolo[5,1-b]-quinazolin-9(4H)-one

A mixture of 3.5 g of 7-chloro-4,9-dihydro-4-methyl-9-oxo-pyrazolo[5,1-b]quinazoline-2-carbonitrile, 2.5 g of sodium azide, 2.1 g of ammonium chloride and 600 ml of dimethylformamide is stirred and heated at 100° C. for 18 hours, then evaporated at reduced pressure, removing about 575 ml of solvent. The residue is poured into excess dilute hydrochloric acid and the resulting solid is collected by filtration and washed with water. The solid is stirred with excess aqueous sodium carbonate and the solution is clarified by filtration. The filtrate is acidified with dilute hydrochloric acid and the resulting precipitate of 7-chloro-4-methyl-2-(1H-tetrazol-5-yl)pyrazolo[5,1-b]quinazolin-9(4H)-one is collected by filtration, washed with water and dried; mp 312° C. (dec), after crystallization from dimethylformamide/ethanol.

By substituting an equivalent amount of 7-chloro-4-ethyl-4,9-dihydro-9-oxo-pyrazolo[5,1-b]quinazoline-2-carbonitrile for the 7-chloro-4,9-dihydro-4-methyl-9-oxo-pyrazolo[5,1-b]quinazoline-2-carbonitrile in the above example, the product is:

7-Chloro-4-ethyl-2-(1H-tetrazol-5-yl)pyrazolo[5,1-b]-quinazolin-9(4H)-one

EXAMPLE 3

7-Fluoro-4-methyl-2-(1H-tetrazol-5-yl)pyrazolo[5,1-b]quinazolin-9(4H)-one

A mixture of 3.0 g of 7-fluoro-4,9-dihydro-4-methyl-9-oxo-pyrazolo-2-carbonitrile and 500 ml of dimethylformamide is stirred and heated at 100° C. for 2 hours, then treated with 1.9 g of ammonium chloride and 2.3 g of sodium azide, and stirred and heated at 100° C. for an additional 18 hours. The mixture is cooled, poured into 2.5 liters of ice water and acidified to pH 2 with concentrated hydrochloric acid. The resulting precipitate of 7-fluoro-4-methyl-2-(1H-tetrazol-5-yl)-pyrazolo[5,1-b]quinazolin-9(4H)-one is collected by filtration, washed with water and dried; mp 350°–360° C., after crystallization from dimethylformamide.

EXAMPLE 4

7-Methoxy-4-methyl-2-(1H-tetrazol-5-yl)pyrazolo[5,1-b]quinazolin-9(4H)-one

A mixture of 2.5 g of 4,9-dihydro-7-methoxy-4-methyl-9-oxo-pyrazolo[5,1-b]quinazoline-2-carbonitrile, 1.9 g of sodium azide, 1.5 g of ammonium chloride and 400 ml of dimethylformamide is stirred and heated at 100° C. for 22 hours, then evaporated at reduced pressure. The residue is stirred with 100 ml of tetrahydrofuran and the mixture is diluted with 1 liter of ice water. The resulting solid is collected by filtration, washed with water and dissolved in 300 ml of 0.5 N aqueous sodium hydroxide. The solution is clarified by filtration and the filtrate is acidified with concentrated hydrochloric acid. The resulting precipitate of 7-methoxy-4-methyl-2-(1H-tetrazol-5-yl)pyrazolo[5,1-b]-quinazolin-9(4H)-one is collected by filtration, washed with water and dried; mp 287°–288° C., after crystallization from dimethylformamide/ethanol.

By substituting an equivalent amount of 4,9-dihydro-4,7-dimethyl-9-oxo-pyrazolo[5,1-b]quinazoline-2-carbonitrile for the 4,9-dihydro-7-methoxy-4-methyl-9-oxo-pyrazolo[5,1-b]quinazoline-2-carbonitrile in the above example, the product is:

4,7-Dimethyl-2-(1H-tetrazol-5-yl)pyrazolo[5,1-b]-quinazolin-9(4H)-one

EXAMPLE 5

Method A:

4,9-Dihydro-4-methyl-9-oxo-pyrazolo-[5,1-b]-quinazoline-2-carboxylic Acid, Ethyl Ester.

A stirred suspension of 5.3 g of a 50% mineral oil dispersion of sodium hydride in 30 ml of dimethylformamide is treated dropwise at −10° C., under a nitrogen atmosphere, with a solution of 15.6 g of 5-oxo-2-pyrazoline-3-carboxylic acid, ethyl ester, in 65 ml of dimethylformamide. After the evolution of hydrogen ceases, the mixture is stirred for 2 hours while allowing the temperature to rise to +10° C. The mixture is recooled to −10° C. and treated dropwise, with stirring, with a solution of 21.6 g of 90% N-methylisatoic anhydride in 150 ml of dimethylformamide, then stirred for 18 hours while allowing the temperature to rise to 20°–25° C. The mixture is heated at 90° C. for 1 hour, cooled and poured into 3 liters of ice water containing 10 ml of concentrated hydrochloric acid (final pH about 5). The resulting precipitate is collected by filtration and the filtrate is extracted several times with 600 ml portions of dichloromethane. The precipitate is dissolved in 1 liter of dichloromethane and the solution is combined with the above dichloromethane extracts. The combined dichloromethane solution is washed with water, dried and evaporated. The residual oil is triturated with methanol and the resulting solid is collected, dissolved in tetrahydrofuran and the solution is decolorized by passage through an activated magnesium silicate column (Florisil R). The filtrate is concentrated to a small volume, diluted with ethanol and chilled. The resulting crystalline precipitate of 4,9-dihydro-4-methyl-9-oxo-pyrazolo[5,1-b]quinazoline-2-carboxylic acid, ethyl ester is collected by filtration; mp 239°–241° C., after recrystallization from dichloromethane/ethanol.

Method B:

4,9-Dihydro-4-methyl-9-oxo-pyrazolo[5,1-b]-quinazoline-2-carboxylic Acid, Methyl Ester.

A mixture of 2.29 g of 4,9-dihydro-9-oxo-pyrazolo-[5,1-b]quinazoline-2-carboxylic acid, 5.52 g of anhydrous potassium carbonate and 34.2 g of methyl iodide in 100 ml of dimethyl formamide is stirred at room temperature for 3 days. Water is added and the white solid is filtered off to give 2.2 g (86%) of the ester; mp 287°–289° C. (d).

EXAMPLE 6

7-Chloro-4,9-dihydro-4-methyl-9-oxo-pyrazolo[5,1-b]-quinazoline-2-carboxylic Acid, Ethyl Ester By substituting 23.2 g of 5-chloro-N-methylisatoic anhydride for the N-methylisatoic anhydride in Example 5A, there is obtained 7-chloro-4,9-dihydro-4-methyl-9-oxo-pyrazolo[5,1-b]quinazoline-2-carboxylic acid, ethyl ester; mp 272°–274° C., after recrystallization from dichloromethane/ethanol.

EXAMPLE 7

7-Fluoro-4,9-dihydro-4-methyl-9-oxo-pyrazolo[5,1-b]-quinazoline-2-carboxylic Acid, Ethyl Ester By substituting 21.5 g of 5-fluoro-N-methylisatoic anhydride for the N-methylisatoic anhydride in Example 5A, there is obtained 7-fluoro-4,9-dihydro-4-methyl-9-oxo-pyrazolo[5,1-b]quinazoline-2-carboxylic acid, ethyl ester; mp 288°–290° C., after recrystallization from dichloromethane/ethanol.

EXAMPLE 8

4,9-Dihydro-7-methoxy-4-methyl-9-oxo-pyrazolo[5,1-b]-quinazoline-2-carboxylic Acid, Ethyl Ester By substituting 23.1 g of 5-methoxy-N-methylisatoic anhydride for the N-methylisatoic anhydride in Example 5A, there is obtained 4,9-dihydro-7-methoxy-4-methyl-9-oxo-pyrazolo[5,1-b]quinazoline-2-carboxylic acid, ethyl ester; mp 249°–251° C., after recrystallization from dichloromethane/ethanol.

EXAMPLE 9

4,9-Dihydro-4,7-dimethyl-9-oxo-pyrazolo[5,1-b]-quinazoline-2-carboxylic Acid, Ethyl Ester By substituting 21.0 g of N,5-dimethylisatoic anhydride for the N-methylisatoic anhydride in Example 5A, there is obtained, 4,9--dihydro-4,7-dimethyl-9-oxo-pyrazolo[5,1-b]quinazoline-2-carboxylic acid, ethyl ester, mp 250°–252° C., after recrystallization from dichloromethane/ethanol.

EXAMPLE 10

7-Chloro-4-ethyl-4,9-dihydro-9-oxo-pyrazolo[5,1-b]-quinazoline-2-carboxylic Acid, Ethyl Ester By substituting 31.6 g of 5-chloro-N-ethylisatoic anhydride for the N-methylisatoic anhydride in Example 5A, there is obtained 7-chloro-4-ethyl-4,9-dihydro-9-oxo-pyrazolo[5,1-b]quinazoline-2-carboxylic acid, ethyl ester; mp 256°–257° C., after recrystallization from dimethylformamide/methanol.

EXAMPLE 11

4,9-dihydro-5-methoxy-4-methyl-9-oxo-pyrazolo[5,1-b]quinazoline-2-carboxylic Acid A mixture of 4,9-dihydro-5-methoxy-9-oxo-pyrazolo-[5,1-b]quinazoline-2-carboxylic acid, hydrate (1:0.25) (2.64 g; 0.01 mole), anhydrous potassium carbonate (5.52 g; 0.04 mole) and methyl iodide (15 ml) in dimethyl formamide (75 ml) is stirred at room temperature for 2 days. Water is added and the grey solid is filtered off and taken up in 2(N) sodium hydroxide solution (50 ml) and methanol (50 ml). The mixture is heated under reflux for 2 hrs and the methanol is distilled off in vacuo. The aqueous solution is acidified with conc. HCl and the yellow precipitate is collected and recrystallized from methanol (275 ml), water (5 ml). Yield 0.33 g; mp 255° (d).

EXAMPLE 12

4,9-Dihydro-6,7-dimethoxy-4-methyl-9-oxo-pyrazolo[5,1-b]-quinazoline-2-carboxylic Acid From 4,9-dihydro-6,7-dimethoxy-9-oxo-pyrazolo[5,1-b]-quinazoline-2-carboxylic acid (1.5 g; 5.2 mmole), anhydrous potassium carbonate (3.0 g; 22 mmole), methyl iodide (15 ml) and DMF (50 ml), following the procedure of Example 11, there is obtained 4,9-dihydro-6,7-dimethoxy-4-methyl-9-oxo-pyrazolo[5,1-b]quinazoline-2-carboxylic acid, methyl ester (1.8 g); mp 301°–303° (d). The crude methyl ester (1.8 g) is hydrolyzed with 1(N) sodium hydroxide solution (50 ml) as in Example 11 to give 4,9-dihydro-6,7-dimethoxy-4-methyl-9-oxo-pyrazolo-[5,1-b]quinazoline-2-carboxylic acid (0.95 g) mp 284°–5° (d), after crystallization from DMF/methanol.

EXAMPLE 13

4,9-dihydro-9-oxo-5-propoxy-4-propyl-pyrazolo[5,1-b]-quinazoline-2-carboxylic Acid, Hydrate (10:1)

A mixture of 4,9-dihydro-5-hydroxy-9-oxopyrazolo-[5,1-b]quinazoline-2-carboxylic acid, hydrate (1:0.25) (0.74 g; 3 mmole), anhydrous potassium carbonate (2.76 g; 20 mmole) and n-propyl iodide (3 ml) in dimethyl formamide (15 ml) is stirred at room temperature for 4 days. The inorganic solids are filtered off and the filtrate is evaporated to drynss, in vacuo. The residue is taken up in 2(N) sodium hydroxide solution (25 ml) and warmed on a steam bath for 2 hrs. The mixture is allowed to stand at room temperature overnight and then is acidified with conc. HCl. The precipitate is filtered, washed and dried. Yield 0.125 g; mp 179°–83° C.

EXAMPLE 14

4,9-Dihydro-4-methyl-9-oxo-pyrazolo[5,1-b]quinazoline-2-carboxylic Acid

A mixture of 5.8 g of 4,9-dihydro-4-methyl-9-oxo-pyrazolo[5,1-b]quinazoline-2-carboxylic acid, ethyl ester, 50 ml of 1 N aqueous sodium hydroxide and 400 ml of methanol is heated at reflux until complete solution is attained (about 30 minutes). The solution is evaporated at reduced pressure to remove methanol; the residue is diluted with water and acidified with 1 N hydrochloric acid. The resulting precipitate is 4,9-dihydro-4-methyl-9-oxo-pyrazolo[5,1-b]quinazoline-2-carboxylic acid is collected by filtration, washed with water and dried; mp 265° C., after crystallization from dimethylformamide/methanol.

EXAMPLE 15

7-Chloro-4,9-dihydro-4-methyl-9-oxo-pyrazolo[5,1-b]-quinazoline-2-carboxylic Acid From 0.6 g of 7-chloro-4,9-dihydro-4-methyl-9-oxo-pyrazolo[5,1-b]quinazoline-2-carboxylic acid, ethyl ester, 22 ml of 0.1 N aqueous sodium hydroxide and 66 ml of methanol, following the procedure of Example 14, there is obtained 7-chloro-4,9-dihydro-4-methyl-9-oxo-pyrazolo[5,1-b]quinazoline-2-carboxylic acid; mp 280° C., after crystallization from dimethylformamide/methanol.

EXAMPLE 16

4,9-Dihydro-4,7-dimethyl-9-oxo-pyrazolo[5,1-b]-quinazoline-2-carboxylic Acid From 3.5 g of 4,9-dihydro-4,7-dimethyl-9-oxo-pyrazolo[5,1-b]quinazoline-2-carboxylic acid, ethyl ester, 50 ml of 1 N aqueous sodium hydroxide and 200 ml of methanol, following the procedure of Example 14, there is obtained 4,9-dihydro-4,7-dimethyl-9-oxo-pyrazolo[5,1-b]quinazoline-2-carboxylic acid; mp 269° C., after crystallization from dimethylformamide/ ethanol.

EXAMPLE 17

4,9-Dihydro-7-methoxy-4-methyl-9-oxo-pyrazolo[5,1-b]-quinazoline-2-carboxylic Acid From 6.0 g of 4,9-dihydro-7-methoxy-4-methyl-9-oxo-pyrazolo[5,1-b]quinazoline-2-carboxylic acid, ethyl ester, 100 ml of 1 N aqueous sodium hydroxide and 200 ml of methanol following the procedure of Example 14, there is obtained 4,9-dihydro-7-methoxy-4-methyl-9-oxo-pyrazolo[5,1-b]quinazoline-2-carboxylic acid; mp 259° C., after crystallization from dimethylformamide/ethanol.

EXAMPLE 18

7-Fluoro-4,9-dihydro-4-methyl-9-oxo-pyrazolo[5,1-b]-quinazoline-2-carboxylic Acid From 3.5 g of 7-fluoro-4,9-dihydro-4-methyl-9-oxo-pyrazolo[5,1-b]quinazoline-2-carboxylic acid, ethyl ester, 50 ml of 1 N aqueous sodium hydroxide and 175 ml of methanol, following the procedure of Example 14, there is obtained 7fluoro-4,9-dihydro-4-methyl-9-oxo-pyrazolo[5,1-b]quinazoline-2-carboxylic acid; mp 295° C., after crystallization from dimethylformamide/methanol.

EXAMPLE 19

7-Chloro-4-ethyl-4,9-dihydro-9-oxo-pyrazolo[5,1-b]-quinazoline-2-carboxylic Acid From 11.2 g of 7-chloro-4-ethyl-4,9-dihydro-9-oxo-pyrazolo[5,1-b]quinazoline-2-carboxylic acid, ethyl ester, 100 ml of 1 N aqueous sodium hydroxide and 250 ml of methanol, following the procedure of Example 14, there if obtained 7-chloro-4-ethyl-4,9-dihydro-9-oxo-pyrazolo[5,1-b]quinazoline-2-carboxylic acid; mp 267°–268° C. (d), after crystallization from dimethylformamide/methanol.

PREPARATIVE EXAMPLES

Preparative Example 1

4,9-Dihydro-4-methyl-9-oxo-pyrazolo[5,1-b]quinazoline-2-carboxamide

A mixture of 7.3 g of 4,9-dihydro-4-methyl-9-oxo-pyrazolo[5,1-b]quinazoline-2-carboxylic acid and 250 ml of thionyl chloride is stirred and heated at reflux for 3 hours, then evaporated at reduced pressure. The residue, containing the acid chloride, is stirred with 250 ml of 58% aqueous ammonium hydroxide, then allowed to stand at 20°–25° C. for 2 hrs. The resulting precipitate of 4,9-dihydro-4-methyl-9-oxo-pyrazolo[5,1-b]quinazoline-2-carboxamide is collected by filtration, washed with water and dried; mp 327°–330° C., after crystallization from dimethylformamide/ethanol.

PREPARATIVE EXAMPLE 2

7-Chloro-4,9-dihydro-4-methyl-9-oxo-pyrazolo[5,1-b]quinazoline-2-carboxamide

A mixture of 6.0 g of 7-chloro-4,9-dihydro-4-methyl-9-oxo-pyrazolo[5,1-b]quinazoline-2-carboxylic acid and 200 ml of thionyl chloride is stirred and heated at reflux for 3 hrs, then evaporated at reduced pressure. The residue, containing the acid chloride, is cooled to $-10°$ C., treated with 200 ml of 58% aqueous ammonium hydroxide and stirred at 20°–25° C. for 3 hrs. The resulting precipitate of 7-chloro-4,9-dihydro-4-methyl-9-oxo-pyrazolo[5,1-b]quinazoline-2-carboxamide is collected by filtration, washed with water and dried; mp >360° C., after crystallization from dimethylformamide/ethanol.

PREPARATIVE EXAMPLE 3

7-Chloro-4-ethyl-4,9-dihydro-9-oxo-pyrazolo[5,1-b]quinazoline-2-carboxamide

By substituting an equivalent amount of 7-chloro-4-ethyl-4,9-dihydro-9-oxo-pyrazolo[5,1-b]quinazoline-2-carboxylic acid for the 7-chloro-4,9-dihydro-4-methyl-9-oxo-pyrazolo[5,1-b]quinazoline-2-carboxylic acid in the procedure of Preparative Example 2, the product is 7-chloro-4-ethyl-4,9-dihydro-9-oxo-pyrazolo[5,1-b]quinazoline-2-carboxamide.

PREPARATIVE EXAMPLE 4

7-Fluoro-4,9-dihydro-4-methyl-9-oxo-pyrazolo[5,1-b]quinazoline-2-carboxamide

A mixture of 10.3 g of 7-fluoro-4,9-dihydro-4-methyl-9-oxo-pyrazolo[5,1-b]quinazoline-2-carboxylic acid and 450 ml of thionyl chloride is stirred and heated at reflux for 3 hours, then evaporated at reduced pressure. The residue, containing the acid chloride, is stirred with 450 ml of 58% aqueous ammonium hydroxide for 2 hours at 20°–25° C. The resulting precipitate of 7-fluoro-4,9-dihydro-4-methyl-9-oxo-pyrazolo-[5,1-b]quinazoline-2-carboxamide is collected by filtration, washed with water and dried; mp >350° C.

PREPARATIVE EXAMPLE 5

4,9-Dihydro-7-methoxy-4-methyl-9-oxo-pyrazolo[5,1-b]-quinazoline-2-carboxamide

A mixture of 2.9 g of 4,9-dihydro-7-methoxy-4-methyl-9-oxo-pyrazolo[5,1-b]quinazoline-2-carboxylic acid and 100 ml of thionyl chloride is stirred and heated at reflux for 1 hour, then evaporated at reduced pressure. The residue, containing the acid chloride, is stirred with 100 ml of 58% aqueous ammonium hydroxide for 2 hrs at 20°–25° C. The resulting precipitate of 4,9-dihydro-7-methoxy-4-methyl-9-oxo-pyrazolo[5,1-b]quinazoline-2-carboxamide is collected by filtration washed with water and dried mp >300° C.

PREPARATIVE EXAMPLE 6

4,9-Dihydro-4,7-dimethyl-9-oxo-pyrazolo[5,1-b]-quinazoline-2-carboxamide

By substituting an equivalent amount of 4,9-dihydro-4,7-dimethyl-9-oxo-pyrazolo[5,1-quinazoline-2-carboxylic acid for the 4,9-dihydro-7-methoxy-4-methyl-9-oxo-pyrazolo[5,1-b]quinazoline-2-carboxylic acid in Preparative Example 5, there is obtained 4,9-dihydro-4,7-dimethyl-9-oxo-pyrazolo[5,1-b]quinazoline-2-carboxamide.

PREPARATIVE EXAMPLE 7

4,9-Dihydro-4-methyl-9-oxo-pyrazolo[5,1-b]quinazoline-2-carbonitrile

A mixture of 5.3 g of 4,9-dihydro-4-methyl-9-oxo-pyrazolo[5,1-b]quinazoline-2-carboxamide, 5.2 g of thionyl chloride and 65 ml of dimethylformamide is stirred and heated at 57° C. for 18 hrs, then evaporated at reduced pressure. The residue is stirred with 600 ml of water and the resulting solid 4,9-dihydro-4-methyl-9-oxo-pyrazolo[5,1-b]quinazoline-2-carbonitrile is collected by filtration, washed with water and dried; mp 307°–310° C., after crystallization from dimethylformamide/ethanol.

PREPARATIVE EXAMPLE 8

7-Chloro-4,9-dihydro-4-methyl-9-oxo-pyrazolo[5,1-b]-quinazoline-2-carbonitrile

A mixture of 3.0 g of 7-chloro-4,9-dihydro-4-methyl-9-oxo-pyrazolo[5,1-b]quinazoline-2-carboxamide, 1.6 ml of thionyl chloride and 35 ml of dimethylformamide is stirred and heated at 56° C. for 18 hrs, then evaporated at reduced pressure. The residue is stirred with 600 ml of water for 1 hour and the resulting solid 7-chloro-4,9-dihydro-4-methyl-9-oxo-pyrazolo[5,1-b]-quinazoline-2-carbonitrile is collected by filtration, washed with water and dried; mp 350° C., after crystallization from dimethylformamide/ethanol.

PREPARATIVE EXAMPLE 9

7-Chloro-4-ethyl-4,9-dihydro-9-oxo-pyrazolo-[5,1-b]-quinazoline-2-carbonitrile

By substituting an equivalent amount of 7-chloro-4-ethyl-4,9-dihydro-9-oxo-pyrazolo[5,1-b]quinazoline-2-carboxamide for the 7-chloro-4,9-dihydro-4-methyl-9-oxo-pyrazolo[5,1-b]quinzoline-2-carboxamide in the procedure of Preparative Example 8, the product is 7-chloro-4-ethyl-4,9-dihydro-9-oxo-pyrazolo[5,1-b]-quinazoline-2-carbonitrile.

PREPARATIVE EXAMPLE 10

7-Fluoro-4,9-dihydro-4-methyl-9-oxo-pyrazolo[5,1-b]-quinazoline-2-carbonitrile

A mixture of 9.2 g of 7-fluoro-4,9-dihydro-4-methyl-9-oxo-pyrazolo[5,1-b]quinazoline-2-carboxamide, 25 ml of thionyl chloride and 175 ml of dimethylformamide is stirred and heated at 65° C. for 20 hours, then evaporated at reduced pressure. The residue is stirred with 1 liter of ice water and the resulting solid 7-fluoro-4,9- dihydro-4-methyl-9-oxo-pyrazolo[5,1-b]-quinazoline-2-carbonitrile is collected by filtration, washed with water and dried; mp 331°–340° C., after crystallization from dimethylformamide/ethanol.

PREPARATIVE EXAMPLE 11

4,9-Dihydro-7-methoxy-4-methyl-9-oxo-pyrazolo[5,1-b]-quinazoline-2-carbonitrile

Thionyl chloride (1.5 ml) is added slowly, with stirring to 50 ml of dimethylformamide at 0° C. To this solution is added 2.9 g of 4,9-dihydro-7-methoxy-4-methyl-9-oxo-pyrazolo[5,1-b]quinazoline-2-carboxamide and the mixture is stirred and heated at 50° C. for 18 hrs, then evaporated at reduced pressure. The residue is stirred with 600 ml of ice water and the resulting solid 4,9-dihydro-7-methoxy-4-methyl-9-oxo-pyrazolo-[5,1-b]quinazoline-2-carbonitrile is collected by filtration, washed with water and dried; mp 316°–320° C. after crystallization from dimethylformamide/ethanol.

PREPARATIVE EXAMPLE 12

4,9-Dihydro-4,7-dimethyl-9-oxo-pyrazolo[5,1-b]-quinazoline-2-carbonitrile

By substituting an equivalent amount of 4,9-dihydro-4,9-dimethyl-9-oxo-pyrazolo[5,1-b]quinazoline-2-carboxamide for the 4,9-dihydro-7-methoxy-9-oxo-pyrazolo[5,1-b]quinazoline-2-carboxamide in Preparative Example 11, there is obtained 4,9-dihydro-4,7-dimethyl-9-oxo-pyrazolo[5,1-b]quinazoline-2-carbonitrile.

PREPARATIVE EXAMPLE 13

N,5-Dimethylisatoic Anhydride

A solution of 26.6 g of 5-methylisatoic anhydride in 150 ml of dimethylformamide is treated with 17.5 g of anhydrous sodium carbonate, then with 32 g of iodomethane, and the mixture is stirred at 20°–25° C. for 18 hrs. The reaction mixture is poured into 1.25 liter of ice water and the resulting precipitate of N,5-dimethylisatoic anhydride is collected by filtration, washed with water and dried; mp 166°–169° C.

PREPARATIVE EXAMPLE 14

5-Fluoro-N-methylisotoic Anhydride

By substituting 27 g of 5-fluoroisatoic anhydride for the 5-methylisatoic anhydride Preparative Example 13, there is obtained 5-fluoro-N-methylisatoic anhydride; mp 150°–155° C.

We claim:

1. A compound of the formula:

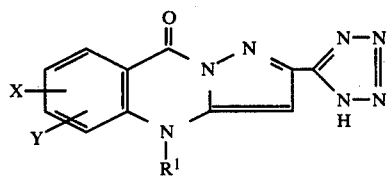

wherein X is hydrogen, hydroxy, alkyl of from 1 to 6 carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is alkyl of from 1 to 6 carbon atoms; and the pharmaceutically acceptable salts thereof.

2. The compound as defined in claim 1 which is 4-methyl-2-(1H-tetrazol-5-yl)pyrazolo[5,1-b]quinazolin-9(4H)-one and the pharmaceutically acceptable salts thereof.

3. The compound as defined in claim 1 which is 7-fluoro-4-methyl-2-(1H-tetrazol-5-yl)pyrazolo[5,1-b]quinazolin-9(4H)-one and the pharmaceutically acceptable salts thereof.

4. The compound as defined in claim 1 which is 7-methoxy-4-methyl-2-(1H-tetrazol-5-yl)pyrazolo[5,1-b]-quinazolin-9(4H)-one and the pharmaceutically acceptable salts thereof.

5. A pharmaceutical composition comprising an anti-allergic effective amount of a compound of the formula II:

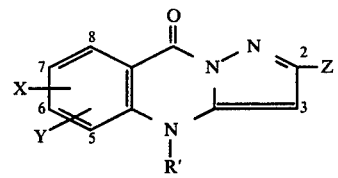

wherein X is hydrogen, hydroxy, alkyl of from 1 to 6 carbon atoms, alkoxy of from 1 to 6 carbon atoms, halo trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is alkyl of from 1 to 6 carbon atoms; Z is COOH or

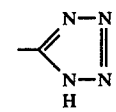

and the pharmaceutically acceptable salts thereof.

6. The pharmaceutical compositions as defined in claim 5 wherein Z is

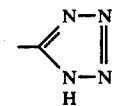

7. The pharmaceutical compositions as defined in claim 5 wherein Z is COOH.

8. A method of preventing the allergic response in a mammal which comprises administering to said mammal an anti-allergic effective amount of a composition as claimed in claim 5.

9. The pharmaceutical composition defined in claim 7 wherein X is methoxy, Y is hydrogen and R' is methyl.

10. The pharmaceutical composition defined in claim 7 wherein X is 5-propoxy, Y is hydrogen and R' is propyl.

11. The pharmaceutical composition defined in claim 7 wherein X is 6-methoxy, Y is 7-methoxy and R' is methyl.

12. The pharmaceutical composition defined in claim 7 wherein X is 5-methoxy, Y is hydrogen and R' is methyl.

13. The pharmaceutical composition defined in claim 7 wherein X is 7-methyl, Y is hydrogen and R' is methyl.

* * * * *